United States Patent
Tai et al.

(10) Patent No.: US 10,183,092 B2
(45) Date of Patent: Jan. 22, 2019

(54) SANITARY ARTICLE AND METHOD FOR MAKING THE SAME

(71) Applicant: KANG NA HSIUNG ENTERPRISE CO., LTD., Tainan (TW)

(72) Inventors: Jung-Chi Tai, Tainan (TW); Ho-Hsi Yang, Tainan (TW); Chun-Meng Huang, Tainan (TW); Chien-Chung Su, Tainan (TW)

(73) Assignee: KANG NA HSIUNG ENTERPRISE CO., LTD., Tainan (TW)

( * ) Notice: Subject to any disclaimer, the term of this patent is extended or adjusted under 35 U.S.C. 154(b) by 272 days.

(21) Appl. No.: 15/045,214

(22) Filed: Feb. 16, 2016

(65) Prior Publication Data

US 2016/0158401 A1    Jun. 9, 2016

Related U.S. Application Data

(62) Division of application No. 14/019,009, filed on Sep. 5, 2013, now abandoned.

(30) Foreign Application Priority Data

Feb. 1, 2013 (TW) .............................. 102104004 A

(51) Int. Cl.
*A61L 15/22* (2006.01)
*A61F 13/534* (2006.01)
(Continued)

(52) U.S. Cl.
CPC ...... *A61L 15/225* (2013.01); *A61F 13/15642* (2013.01); *A61F 13/15658* (2013.01);
(Continued)

(58) Field of Classification Search
CPC ........ A61L 15/225; A61L 15/24; A61L 15/28; A61F 13/534; A61F 13/15642;
(Continued)

(56) References Cited

U.S. PATENT DOCUMENTS 5,489,469 A    2/1996  Kobayashi et al.
6,118,042 A    9/2000  Palumbo
(Continued)

FOREIGN PATENT DOCUMENTS

CN    1511018 A    7/2004
CN    1976658 B    7/2011
(Continued)

OTHER PUBLICATIONS

Search Report dated Apr. 23, 2014 in corresponding European Application No. 12004493.6.
(Continued)

*Primary Examiner* — Vishal I Patel
(74) *Attorney, Agent, or Firm* — Faegre Baker Daniels LLP

(57) ABSTRACT

A sanitary article includes an absorbent pad including an upper sheet layer, a lower sheet layer, and a pulp-and-SAP powder layer combination. The powder layer combination is constituted by alternate layers of pulverized pulp and superabsorbent polymer (SAP) powder. A method for making the sanitary article is also disclosed.

8 Claims, 2 Drawing Sheets

(51) Int. Cl.
*A61F 13/15* (2006.01)
*A61L 15/24* (2006.01)
*A61L 15/28* (2006.01)
*A61F 13/53* (2006.01)

(52) U.S. Cl.
CPC ............ *A61F 13/534* (2013.01); *A61L 15/24* (2013.01); *A61L 15/28* (2013.01); *A61F 2013/530532* (2013.01); *A61F 2013/530547* (2013.01)

(58) Field of Classification Search
CPC .... A61F 13/15658; A61F 2013/530532; A61F 2013/530547
See application file for complete search history.

(56) References Cited

U.S. PATENT DOCUMENTS

| | | | |
|---|---|---|---|
| 6,258,996 B1 | 7/2001 | Goldman | |
| 6,485,667 B1 * | 11/2002 | Tan ................... | A61F 13/15203 264/112 |
| 2002/0133131 A1 * | 9/2002 | Rangachari ....... | A61F 13/15203 604/370 |
| 2003/0084983 A1 | 5/2003 | Rangachari et al. | |
| 2003/0195485 A1 | 10/2003 | Rangachari et al. | |
| 2004/0019338 A1 | 1/2004 | Litvay et al. | |
| 2006/0069367 A1 | 3/2006 | Waksmundzki et al. | |
| 2006/0173433 A1 | 8/2006 | Laumer et al. | |
| 2007/0043330 A1 | 2/2007 | Lankhof et al. | |
| 2007/0088301 A1 | 4/2007 | Ikeda | |
| 2007/0112319 A1 | 5/2007 | Guidotti | |
| 2007/0255243 A1 | 11/2007 | Kaun et al. | |
| 2008/0172017 A1 | 7/2008 | Carlucci et al. | |
| 2009/0270823 A1 | 10/2009 | Meizelman | |
| 2010/0305536 A1 | 12/2010 | Fernkvist et al. | |
| 2011/0152806 A1 | 6/2011 | Zhou | |
| 2013/0139960 A1 | 6/2013 | Maruyama et al. | |

FOREIGN PATENT DOCUMENTS

| | | |
|---|---|---|
| CN | 102700179 A | 10/2012 |
| JP | 2004535842 A | 12/2004 |
| JP | 2005-533571 A | 11/2005 |
| JP | 2008-231619 A | 10/2008 |
| JP | 2009-114555 A | 5/2009 |
| JP | 2012-016584 A | 1/2012 |

OTHER PUBLICATIONS

Search Report for Taiwan Patent Application No. 102104004, dated Jun. 10, 2015, with English Language translation.
Search Report for Chinese Patent Application No. 2013101215608, dated Dec. 31, 2014, with English Language translation.

* cited by examiner

SANITARY ARTICLE AND METHOD FOR MAKING THE SAME

CROSS-REFERENCE TO RELATED APPLICATION

This application is a division of U.S. patent application Ser. No. 12/887,931, entitled VEHICLE WHEELCHAIR LIFT and filed Sep. 22, 2010, which claims priority of Taiwanese Application No. 102104004, filed Feb. 1, 2013, the entire disclosures of which are hereby expressly incorporated herein by reference.

BACKGROUND OF THE INVENTION

1. Field of the Invention

This invention relates to a sanitary article, particularly to a sanitary article for absorbing a body fluid and a method for making the same.

2. Description of the Related Art

A sanitary article, especially a sanitary napkin for night use, normally has a thickness larger than 5 mm, and is therefore bulky and not comfortable to wear.

In a conventional sanitary article, a mixture of pulverized pulp and superabsorbent polymer (SAP) powder is used to form an absorbent body. The provision of the bulky pulverized pulp facilitates the flow of liquid in the absorbent body so as to prevent the liquid from accumulating at a specific region of the absorbent body. This is the reason why the thickness of the absorbent body cannot be considerably reduced.

On the other hand, if the percentage of the SAP powder in the absorbent body is increased, the SAP powder cannot be properly confined by the pulverized pulp. Thus, the SAP powder and pulverized pulp need to be further mixed with thermo-melting composite fibers, and then subjected to a heating treatment so as to bind the SAP powder in the absorbent body. However, the introduction of the composite fibers considerably reduces the absorption ability of the SAP powder.

U.S. Pat. No. 5,284,610 discloses a high molecular absorbent sheet manufacturing process which includes sending paper pulp and a high molecular absorbent compound to a trough for mixing by wired cylinders and spreading over a conveyer system, drying the mixture carried on the conveyer system, and squeezing the dried mixture into a roll of high molecular absorbent sheet through two matched hot impression cylinders.

SUMMARY OF THE INVENTION

An object of the present invention is to provide a sanitary article and a method for making the same. The sanitary article made by the method of this invention has an unexpected excellent absorption ability in comparison with conventional sanitary articles, and has a thickness less than 5 mm.

According to a first aspect of this invention, a method for making a sanitary article includes the following steps:

(a) providing a loading route which includes a plurality of zones arranged in series in a linear direction;

(b) providing a conveying web member which includes a plurality of loading regions that are displaced from each other in the linear direction;

(c) causing the conveying web member to move along the linear direction such that each of the loading regions sequentially passes through the plurality of zones;

(d) sprinkling a first fraction of a predetermined amount of pulverized pulp onto a respective one of the loading regions when the respective one of the loading regions is being moved through a first one of the plurality of zones so as to form a first pulp layer on the respective one of the loading regions;

(e) sprinkling a first fraction of a predetermined amount of superabsorbent polymer (SAP) powder onto the first pulp layer when the respective one of the loading regions loaded with the first pulp layer is being moved through a second one of the plurality of zones so as to form a first SAP layer on the first pulp layer;

(f) sprinkling a second fraction of the predetermined amount of the pulverized pulp onto the first SAP layer when the respective one of the loading regions loaded with the first pulp layer and the first SAP layer is being moved through a third one of the plurality of zones so as to form a second pulp layer on the first SAP layer;

(g) sprinkling a second fraction of the predetermined amount of the SAP powder onto the second pulp layer when the respective one of the loading regions loaded with the second pulp layer, the first SAP layer, and the first pulp layer is being moved through a fourth one of the plurality of zones so as to form a second SAP layer on the second pulp layer, thereby forming a transferable pulp-and-SAP powder layer combination; and (h) transferring the transferable pulp-and-SAP powder layer combination so as to permit the transferable pulp-and-SAP powder layer combination to be sandwiched between upper and lower sheets.

According to a second aspect of this invention, a sanitary article includes an absorbent pad which includes an upper sheet layer, a lower sheet layer, and a pulp-and-SAT powder layer combination sandwiched between the upper and lower sheet layers. The pulp-and-SAP powder layer combination is made by the following steps of:

(i) sprinkling a first fraction of a predetermined amount of pulverized pulp to form a first pulp layer;

(ii) sprinkling a first fraction of a predetermined amount of superabsorbent polymer (SAP) powder onto the first pulp layer so as to form a first SAP layer on the first pulp layer;

(iii) sprinkling a second fraction of the predetermined amount of the pulverized pulp onto the first SAP layer as to form a second pulp layer on the first SAP layer;

(iv) sprinkling a second fraction of the predetermined amount of the SAP powder onto the second pulp layer so as to form a second SAP layer on the first pulp layer; and (v) sprinkling a third fraction of the predetermined amount of the pulverized pulp onto the second SAP layer so as to form a third pulp layer on the second SAP layer, thereby forming the pulp-and-SAP powder layer combination.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
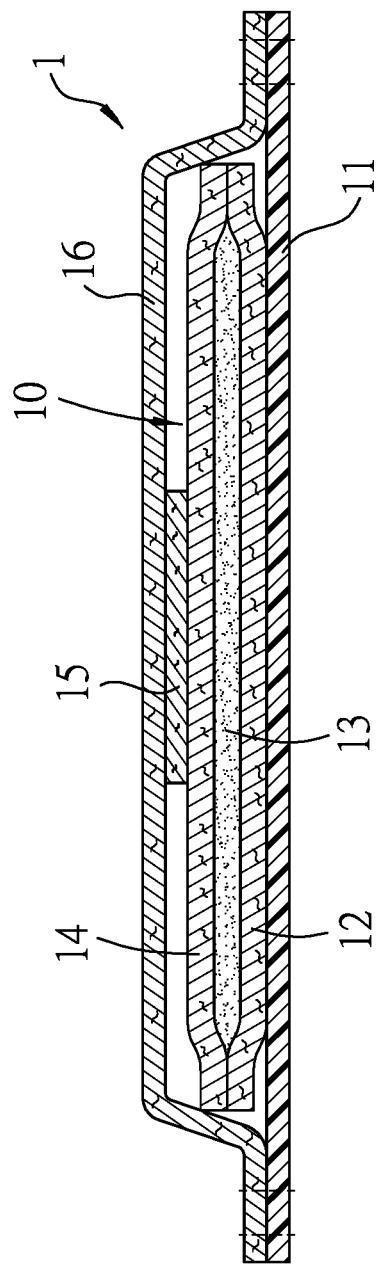
FIG. 1 is a cross-sectional view of the preferred embodiment of a sanitary article according to this invention.

Referring to FIG. 1, the preferred embodiment of a sanitary article (sanitary napkin) according to this invention includes an absorbent pad 10, a liquid-permeable layer 16 disposed on an upper side of the absorbent pad 10, a liquid-impermeable layer 11 disposed on a lower side of the absorbent pad 10, and an absorbent enhancement layer 15 disposed between the absorbent pad 10 and the liquid-permeable layer 16.

The absorbent pad 10 and the absorbent enhancement layer 15 are enclosed between the liquid-permeable layer 16 and the liquid-impermeable layer 11. The absorbent enhancement layer 15 is made of a water-absorbent material and can rapidly absorb a body fluid and transfer the fluid to the absorbent pad 10. Preferably, the absorbent enhancement layer 15 is preferably made from cellulose/cotton paper or composite fibers. The composite fibers may be made from a copolymer of polypropylene and polyethylene, or a copolymer of polyethylene terephthalate and polyethylene.

The liquid-impermeable layer 11 is a liquid-impermeable plastic substrate to prevent leakage of the body fluid, and is made of, for example, polyethylene. The liquid-permeable layer 16 is disposed to directly contact the skin of a user, and is preferably made of a liquid-permeable non-woven fabric (such as polyethylene/polyethylene terephthalate (PE/PET) composite fibers or polyethylene/polypropylene (PE/PP) composite fibers). In addition, the liquid-permeable layer 16 may include some additives, such as aloe vera, vitamin E, a lubricant, an antibacterial agent, and any other additives that can help keep the skin surface of the user in a comfortable condition.

Figure 2:
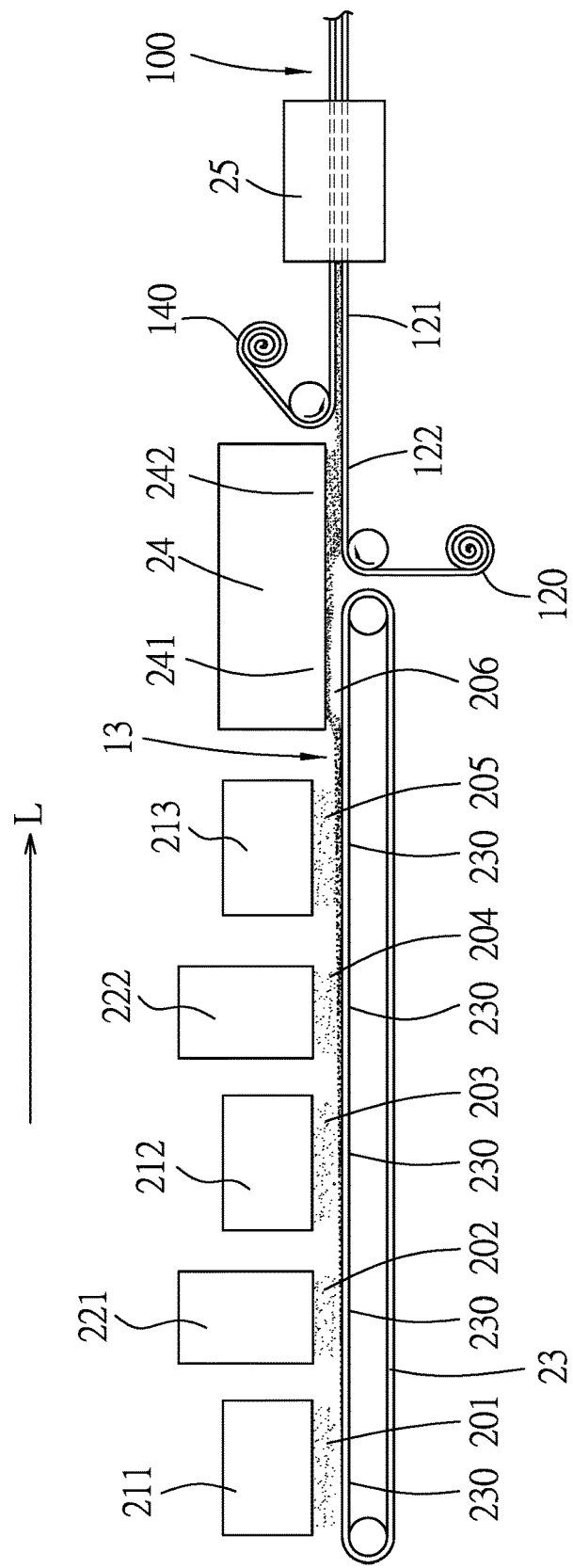
FIG. 2 is a flow diagram illustrating the preferred embodiment of a method for making the sanitary article according to this invention.

The preferred embodiment of a method for making the sanitary article, especially the absorbent pad 10, is shown in FIG. 2. The method includes the following steps A to K.

In step A, a loading route is provided. The loading route includes a plurality of zones arranged in series in a linear direction (L). In this embodiment, first to sixth zones 201, 202, 203, 204, 205, 206 are provided.

In step B, a conveying web member 23 is provided. The conveying web member 23 includes a plurality of loading regions 230 that are displaced from each other in the linear direction (L). In the preferred embodiment, the conveying web member 23 is a looped conveying belt.

In step C, the conveying web member 23 is caused to move along the linear direction (L) such that each of the loading regions 230 sequentially passes through the first to sixth zones 201, 202, 203, 204, 205, 206.

In step D, a first pulp sprinkler 211 is used to sprinkle a first fraction of a predetermined amount of pulverized pulp onto a respective one of the loading regions 230 when the respective one of the loading regions 230 is being moved through the first zone 201 so as to form a first pulp layer on the respective one of the loading regions 230. In the preferred embodiment, the pulverized pulp is in dry form.

In step E, a first SAP sprinkler 221 is used to sprinkle a first fraction of a predetermined amount of superabsorbent polymer (SAP) powder onto the first pulp layer when the respective one of the loading regions 230 loaded with the first pulp layer is being moved through the second zone 202 so as to form a first SAP layer on the first pulp layer. The SAP powder may include a powder material selected from poly (acrylic acid) polyacrylamide, or polyethylene alcohol.

In step F, a second pulp sprinkler 212 is used to sprinkle a second fraction of the predetermined amount of the pulverized pulp onto the first SAP layer when the respective one of the loading regions 230 loaded with the first pulp layer and the first SAP layer is being moved through the third zone 203 so as to form a second pulp layer on the first SAP layer.

In step G, a second SAP sprinkler 222 is used to sprinkle a second fraction of the predetermined amount of the SAP powder onto the second pulp layer when the respective one of the loading regions 230 loaded with the second pulp layer, the first SAP layer, and the first pulp layer is being moved through the fourth zone 204 so as to form a second SAP layer on the second pulp layer.

In step H, a third pulp sprinkler 213 is used to sprinkle a third fraction of the predetermined amount of the pulverized pulp onto the second SAP layer when the respective one of the loading regions 230 loaded with the first and second pulp layers and the first and second SAP layers is being moved through the fifth zone 205 so as to form a third pulp layer, thereby forming a transferable pulp-and-SAP powder layer combination 13. It should be noted that although the loading route in this preferred embodiment includes six zones 201, 202, 203, 204, 205, 206, the number of zones may vary.

In step I, the transferable pulp-and-SAP powder layer combination 13 is transferred so as to be sandwiched between upper and lower sheets 140, 120. Each of the upper and lower sheets 140, 120 is made of a water-absorbent material, and is preferably made from cellulose/cotton paper or composite fibers. The composite fibers may be made from a copolymer of polypropylene and polyethylene, or a copolymer of polyethylene terephthalate and polyethylene. The materials of the upper and lower sheets 140, 120 can be the same or different.

In this preferred embodiment, step I includes the following substeps: (I1) advancing the lower sheet 120 in the linear direction (L) downstream of the sixth zone 206; (I2) advancing the upper sheet 140 in the linear direction (L) such that the upper sheet 140 covers a leading segment 121 of the lower sheet 120 while leaving a trailing segment 122 of the lower sheet 120 uncovered by the upper sheet 140; and (I3) transferring the transferable pulp-and-SAP powder layer combination 13 by suction to the trailing segment 122 of the lower sheet 120 so as to be advanced therewith to be sandwiched between the upper and lower sheets 140, 120.

Specifically, the transferable pulp-and-SAP powder layer combination 13 is transferred using a transferring device 24 that extends from the sixth zone 206 to the trailing segment 122 of the lower sheet 120, and which includes a conveying rigid member (not shown) including a plurality of rigid areas (not shown) that are displaced from each other in the linear direction (L). Each of the rigid areas is formed with a suction hole (not shown) extending through the rigid area, and a wire screen (not shown) fully covering the suction hole. The suction hole can be configured to have a desired hole shape. The wire screen has a mesh size smaller than the particle size of the pulverized pulp and the SAP powder. The transferring device 24 has first and second sections 241, 242. In operation, the conveying rigid member is caused to move along the linear direction (L) such that each of the rigid areas sequentially passes through the first and second sections 241, 242. When a respective one of the rigid areas is being moved to the first section 241, the transferable pulp-and-SAP powder layer combination 13 being moved on the conveying web member 23 to the sixth zone 206 is suctioned up to cover the suction hole of the respective one of rigid areas, and hence assumes a shape substantially consistent with the hole shape of the suction hole. When the respective one of the rigid areas is being moved to the second section 242, the transferable pulp-and-SAP powder layer combination 13 is released and falls onto the trailing segment 122 of the lower sheet 120, whereby the transferable pulp-and-SAP powder layer combination 13 having a desired shape can be disposed on the lower sheet 120. By virtue of the above steps A to I, a plurality of the transferable pulp-and-SAP powder layer combinations 13 are transferred so as to be sandwiched between the upper and lower sheets 140, 120.

In step J, the upper and lower sheets 140, 120 with the transferable pulp-and-SAP powder layer combinations 13 sandwiched therebetween are pressed together using a pressing device 25 to thereby obtain an absorbent laminate 100. The absorbent laminate 100 has a thickness ranging from 0.5 mm to 3 mm. It should be noted because no thermo-melting material is added to the transferable pulp-and-SAP powder layer combination 13, step J can be implemented at room temperature or at a relatively high temperature. In the preferred embodiment, step J is implemented at room temperature, so that the absorption ability of the SAP powder will not be adversely affected or compromised.

In step K, the absorbent laminate 100 is cut to form a plurality of the absorbent pads 10, each of which includes an upper sheet layer 14, a lower sheet layer 12, and the transferable pulp-and-SAP powder layer combination 13. It should be noted that because the transferable pulp-and-SAP powder layer combination 13 is formed into a specific shape consistent with the hole shape of the suction hole, it can be properly enclosed between the upper and lower sheet layers 14, 12 and the pulverized pulp and the SAP powder therein are less likely to escape therefrom during the cutting step. Furthermore, since the transferable pulp-and-SAP powder layer combination 13 is enclosed between the upper and lower sheet layers 14, 12, it is not necessary to add thermo-melting material for binding the SAP powder.

In this preferred embodiment, based on a total weight of each of the absorbent pads 10, each of the absorbent pads 10 has the pulverized pulp in an amount ranging from 25 wt % to 65 wt %, and the SAP powder in an amount ranging from 5 wt % to 65 wt %.

In the case that each of the upper and lower sheet layers 14, 12 of the absorbent pad 10 is made from cellulose/cotton paper, based on a total weight of the absorbent pad 10, the upper and lower sheet layers 14, 12 have a weight percentage ranging from 10 wt % to 25 wt %, the pulverized pulp is in an amount ranging from 25 wt % to 60 wt %, and the SAP powder is in an amount ranging from 15 wt % to 65 wt %.

In the case that each of the upper and lower sheet layers 14, 12 of the absorbent pad 10 is made from composite fibers, based on a total weight of the absorbent pad 10, the upper and lower sheet layers 14, 12 have a weight percentage ranging from 5 wt % to 30 wt %, the pulverized pulp is in an amount ranging from 35 wt % to 65 wt %, and the SAP powder is in an amount ranging from 5 wt % to 60 wt %.

It should be noted that, in the conventional sanitary napkins, the ratio of the pulverized pulp and the SAP powder is about 10:1. In the method according to this invention, the ratio of the pulverized pulp and the SAP powder can be approximately 1:1. Because the amount of the pulverized pulp is reduced, the thickness and weight of the sanitary article of this invention can be greatly reduced.

In addition, in the method of this invention, since the pulverized pulp is in dry form, as is the SAP powder, a drying (heating) process is not necessary. It is found that when the pulverized pulp is in dry form, the sanitary article has an unexpected excellent absorption ability. Thus, the method of this invention is suitable for producing a sanitary napkin for night use, which may have a length ranging from 35 cm to 50 cm.

EXAMPLE 1

A sanitary napkin as shown in FIG. 1 was produced. The sanitary napkin had a thickness of 3 mm, a weight of 12.5 g, and a length of 36.5 cm, and included a liquid-permeable layer 16 made from PE/PET composite fiber (FAR EASTERN, Taiwan), a liquid-impermeable layer 11 which was a polyethylene film (commercially available from Tai-Young Film Co., Ltd., Taiwan), an absorbent enhancement layer 15 which was a SMS nonwoven fabric commercially available from Universal Incorporation, Taiwan), and an absorbent pad 10 made by the method of this invention. The absorbent pad 10 had upper and lower sheet layers 14, 12 each being made from cellulose paper (commercially available from Union Paper Corporation, Taiwan), and a pulp-and-SAP powder layer combination 13, which included pulverized pulp (commercially available from Weyerhaeuser, USA), and SAP powder (poly (acrylic acid), commercially available from Sumitomo Chemical Co., Ltd., Japan). Based on a total weight of the absorbent pad 10, the upper and lower sheet layers 14, 12 had a weight percentage of 19 wt %, the pulverized pulp was in an amount of 39 wt %, and the SAP powder was in an amount of 42 wt %.

EXAMPLE 2

A sanitary napkin of Example 2 was made according the procedures employed for making that of Example 1, except that the sanitary napkin of Example 2 had a weight of 13.9 g and a length of 40.0 cm.

Absorbency Test

To demonstrate the superior absorption ability of the sanitary article according to the present invention, the sanitary napkins of Examples 1 and 2 and commercially available sanitary napkins were subjected to an absorbency test. In this test, each of the sanitary napkins was weighed to obtain a dry weight (W0), and was then immersed in pure water until fully saturated. Thereafter, the sanitary napkin was removed and allowed to drip until dripping stopped. The wet sanitary napkin was then weighed to obtain a wet weight (W1). The absorption ability of each of the sanitary napkins was represented by the following equation (I). The greater the value, the better the absorption ability.

$$\text{Absorption ability} = W1/W0 \tag{I}$$

The test results are shown in Table 1.

TABLE 1

| Sanitary napkin (Product name) | Length (cm) | Weight (g) | Absorption ability |
|---|---|---|---|
| Kao, Laurier, Safety Comfort Night Slim Wing | 35.0 | 15.1 | 19.0 |
| Kao, Laurier, Safety Comfort with Gathers | 40.0 | 17.3 | 18.0 |
| P&G, Whisper, Soft & Dry | 36.0 | 18.9 | 11.2 |
| P&G, Whisper, Soft & Dry | 40.0 | 23.3 | 10.8 |
| Unicharm, Sofy, Ultra-deep Sleep | 35.0 | 15.6 | 31.8 |
| Unicharm, Sofy, Ultra-deep Sleep | 41.0 | 16.4 | 28.6 |

TABLE 1-continued

| Sanitary napkin (Product name) | Length (cm) | Weight (g) | Absorption ability |
| --- | --- | --- | --- |
| Kotex, Natural Herbal Slim | 35.0 | 17.1 | 29.4 |
| Kotex, Natural Herbal Slim | 41.0 | 23.2 | 33.9 |
| Carnation, Panty Liner, Lightweight and Highly Absorbent | 36.5 | 18.1 | 19.6 |
| Carnation, Panty Liner, Lightweight and Highly Absorbent | 40.0 | 20.8 | 19.0 |
| Example 1 | 36.5 | 12.5 | 48.3 |
| Example 2 | 40.0 | 13.9 | 49.8 |

From the results shown in Table 1, it was found that, compared with the commercially available sanitary napkins, the sanitary napkins of Examples 1 and 2 had lighter weights and better absorption ability.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A method for making a sanitary article, comprising the following steps:
   (a) providing a loading route which includes a plurality of zones arranged in series in a linear direction;
   (b) providing a conveying web member which includes a plurality of loading regions that are displaced from each other in the linear direction;
   (c) causing the conveying web member to move along the linear direction such that each of the loading regions sequentially passes through the plurality of zones;
   (d) sprinkling a first fraction of a predetermined amount of pulverized pulp onto a respective one of the loading regions when the respective one of the loading regions is being moved through a first one of the plurality of zones so as to form a first pulp layer on the respective one of the loading regions;
   (e) sprinkling a first fraction of a predetermined amount of superabsorbent polymer (SAP) powder onto the first pulp layer when the respective one of the loading regions loaded with the first pulp layer is being moved through a second one of the plurality of zones so as to form a first SAP layer on the first pulp layer;
   (f) sprinkling a second fraction of the predetermined amount of the pulverized pulp onto the first SAP layer when the respective one of the loading regions loaded with the first pulp layer and the first SAP layer is being moved through a third one of the plurality of zones so as to form a second pulp layer on the first SAP layer;
   (g) sprinkling a second fraction of the predetermined amount of the SAP powder onto the second pulp layer when the respective one of the loading regions loaded with the second pulp layer, the first SAP layer, and the first pulp layer is being moved through a fourth one of the plurality of zones so as to form a second SAP layer on the second pulp layer, thereby forming a transferable pulp-and-SAP powder layer combination; and
   (h) transferring the transferable pulp-and-SAP powder layer combination by suction so as to permit the transferable pulp-and-SAP powder layer combination to be sandwiched between upper and lower sheets;
   wherein the pulverized pulp and the SAP powder in the transferable pulp-and-SAP powder layer combination are in dry form, and
   step (h) includes the following substeps:
   (h1) advancing the lower sheet in the linear direction downstream of the fourth one of the plurality of zones;
   (h2) advancing the upper sheet in the linear direction such that the upper sheet covers a leading segment of the lower sheet while leaving a trailing segment of the lower sheet uncovered by the upper sheet; and
   (h3) transferring the transferable pulp—and—SAP powder layer combination by suction to the trailing segment of the lower sheet so as to be advanced therewith to be sandwiched between the upper and lower sheets.

2. The method of claim 1, further comprising a step (i) of pressing together the upper and lower sheets with the transferable pulp-and-SAP powder layer combination sandwiched therebetween into an absorbent laminate.

3. The method of claim 2, wherein step (i) is implemented at room temperature.

4. The method of claim 2, wherein the absorbent laminate has a thickness ranging from 0.5 mm to 3 mm.

5. The method of claim 2, further comprising a step (j) of cutting the absorbent laminate into a plurality of absorbent pads.

6. The method of claim 5, wherein, based on a total weight of each of the absorbent pads, each of the absorbent pads has the pulverized pulp in an amount ranging from 25 wt % to 65 wt %, and the SAP powder in an amount ranging from 5 wt % to 65 wt %.

7. The method of claim 2, further comprising, between steps (g) and (h), a step (k) of sprinkling a third fraction of the predetermined amount of the pulverized pulp onto the second SAP layer when the respective one of the loading regions loaded with the first and second pulp layers and the first and second SAP layers is being moved through a fifth one of the plurality of zones so as to form a third pulp layer, such that the transferable pulp-and-SAP powder layer combination includes the first, second and third pulp layers and the first and second SAP layers.

8. The method of claim 1, wherein each of the upper and lower sheets is made of a water-absorbent material.

* * * * *